United States Patent [19]
Kushner

[11] Patent Number: 5,516,286
[45] Date of Patent: May 14, 1996

[54] DENTAL ISOLATION TRAY PARTICULARLY SUITED FOR USE WHEN APPLYING DENTAL SEALANTS AND METHOD FOR ITS USE

[76] Inventor: Philip Kushner, 8 Miller Farms Dr., Miller Place, N.Y. 11746

[21] Appl. No.: 243,173

[22] Filed: May 16, 1994

[51] Int. Cl.$^6$ ..................................................... A61C 17/06
[52] U.S. Cl. ............................................. 433/93; 433/136
[58] Field of Search ............................... 433/93, 94, 136, 433/138, 140

[56] References Cited

U.S. PATENT DOCUMENTS

| | | | |
|---|---|---|---|
| 1,498,219 | 6/1924 | Williams | 433/140 |
| 1,986,275 | 1/1935 | Lowry | 433/136 |
| 2,637,107 | 5/1953 | Daigle | 433/136 |
| 2,701,916 | 2/1955 | Jarboe . | |
| 2,823,455 | 2/1958 | Sprague | 433/140 |
| 2,873,528 | 2/1959 | Thompson . | |
| 3,049,806 | 8/1962 | Cofresi . | |
| 3,396,468 | 8/1968 | Dayhoff . | |
| 3,772,790 | 11/1973 | Swann-Gett et al. . | |
| 4,259,067 | 3/1981 | Nelson | 433/93 |
| 4,260,378 | 4/1981 | O'Neil | 433/93 |
| 5,276,068 | 1/1994 | Waknine | 433/228.1 |

OTHER PUBLICATIONS

Christensen, Gordon J. "Using Rubber Dams to Boost Quality, Quantity of Restorative Services," *Journal of American Dental Association*, v. 125 (Jan. 1994): 81–82.

Park, Kitae and Penugonda, Bapanaiah. "Pit and Fissure Sealants," *New York State Dental Journal* (Apr., 1991).

"Top Dental Products,"*Dental Products Report* (Dec., 1993):3–4.

Advertising Slick for "Handidam."

*Primary Examiner*—Cary E. O'Connor
*Attorney, Agent, or Firm*—Galgano & Burke

[57] ABSTRACT

A dental isolation tray has an outer side wall, an inner side wall, and a roof which joins the inner and outer side walls. An aspiration conduit having spaced apart aspiration ports is molded into the peripheral edges of the side walls and into the interface between the interior side wall and the roof. An aspiration coupling is provided for fluidly connecting the aspiration conduit with a suction tube. A portion of the roof and outer side wall is pre-cut to expose the occlusal and buccal aspects of preselected teeth. An adjustable bite block is mounted on or adjacent to the roof of the tray and extends substantially perpendicular to the roof of the tray. The full arch tray may have one or two quadrants cut-out and may be placed on either the upper or the lower arch to completely cover the arch and associated alveolar ridge. A single quadrant tray may be formed as either a left hand tray or a right hand tray and can also be placed over either upper or lower arches. The tray is dimensioned to provide relatively generous spacing between the side walls and the teeth so that the lingual aspect of the teeth which are exposed by the cut-out are accessible while still being isolated from the patient's tongue.

25 Claims, 3 Drawing Sheets

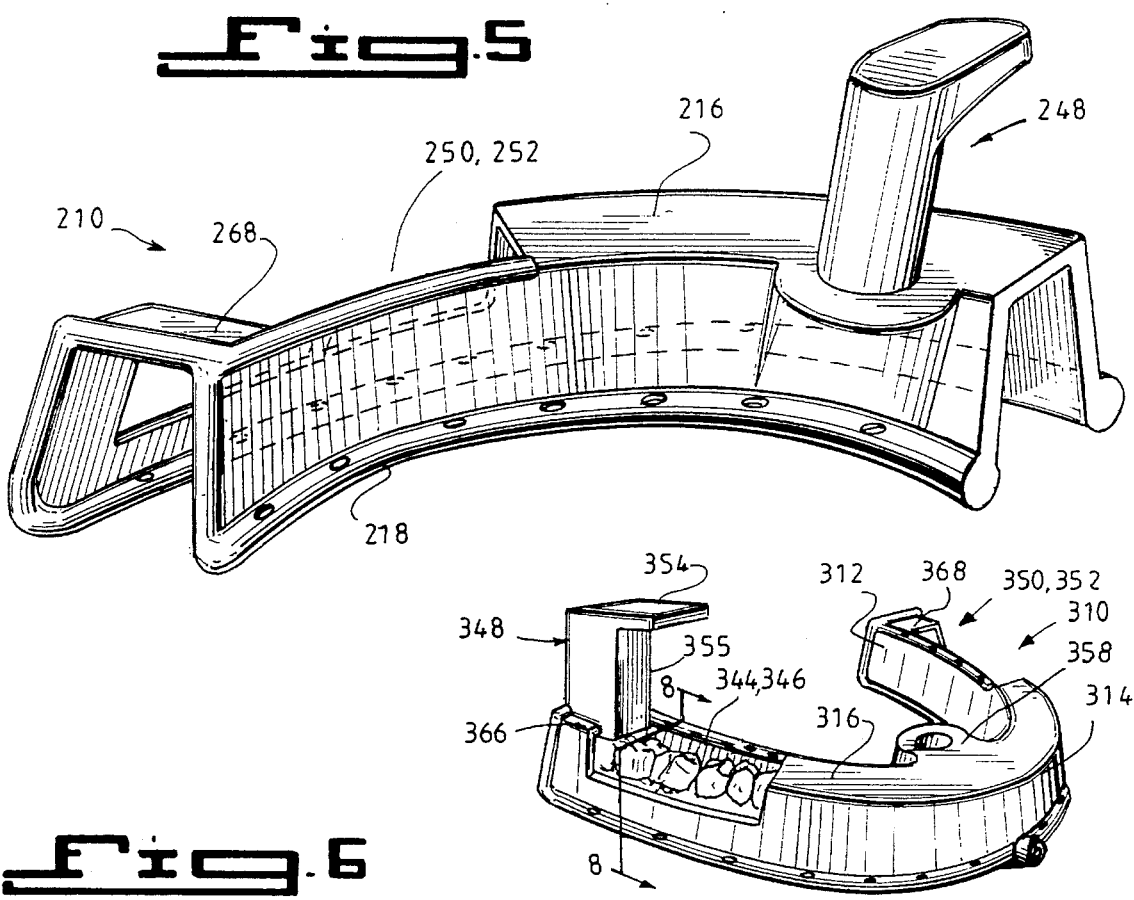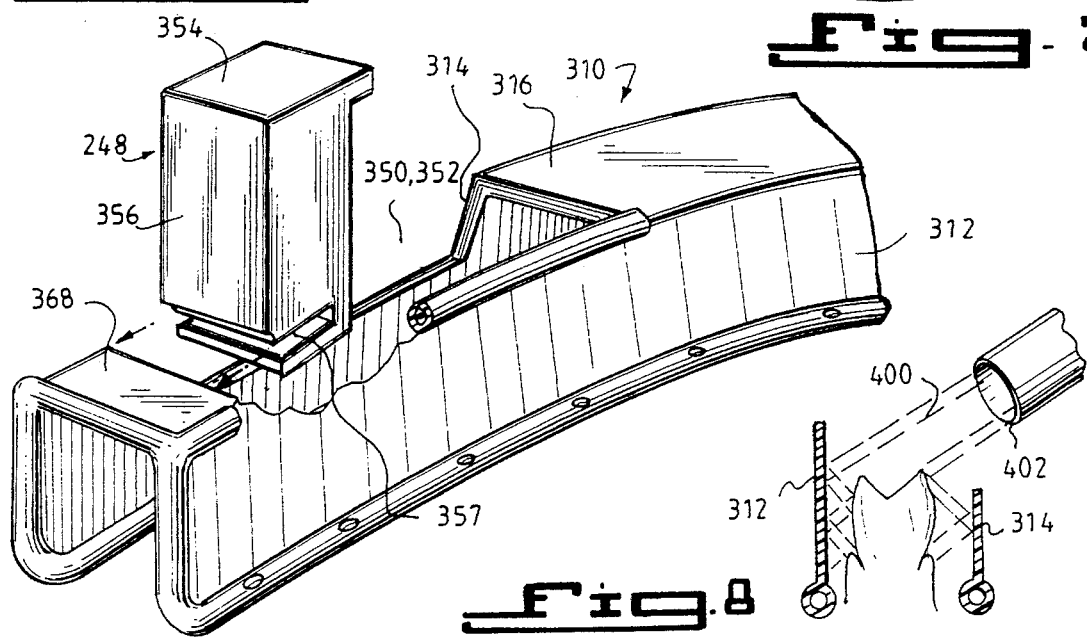

DENTAL ISOLATION TRAY PARTICULARLY SUITED FOR USE WHEN APPLYING DENTAL SEALANTS AND METHOD FOR ITS USE

BACKGROUND OF THE INVENTION

1. Field of the Invention

The invention relates to a dental isolation tray. More particularly, the invention relates to an isolation tray which is particularly suited for use when applying a dental sealant.

2. State of the Art

Dental sealants have been studied for many years and all studies have shown that the application of dental sealants to bicuspid and molar fissures is extremely effective in preventing tooth decay. Nevertheless, the procedure of applying dental sealants is still greatly under-utilized by dentists. The reason why most dentists do not utilize the procedure is that it is extremely difficult to perform properly and it is common to see multiple failures shortly after treatment. See, e.g., New York State Dental Journal, April 1992.

A dental sealant is a bonding liquid plastic resin which is applied to fissures in posterior teeth to seal them and thus prevent decay. The sealant is typically and economically applied to a contiguous group (quadrant) of teeth at the same time. However, it is critical that these teeth be isolated from the other teeth and kept scrupulously clean and dry during the application of the sealant. Achieving adequate isolation and dryness is very difficult. This is particularly so when treating children. Children generate more saliva than adults during dental procedures, they have a smaller mouth, and are not likely to remain still during a lengthy procedure. Commonly used devices such as cotton rolls and suction tubes do not provide adequate isolation or desiccation and they are unstable.

Rubber dental dams are well known for use in a variety of dental procedures. However, dental dams are also under-utilized because their use is time consuming, irritating and painful for the patient, and involves additional cost. See, e.g., Journal of the American Dental Association, Vol. 125, pages 81–82 (January 1994). The typical rubber dental dam is simply a rubber mat which is folded and inserted into a patient's mouth. Before insertion, a hole is punched in the rubber mat so that a particular tooth or group of teeth will be exposed when the mat is inserted. The inserted rubber mat is held in position by a frame or a clamp or a combination of frames and clamps. The dental dam covers the patient's tongue, the roof of the patient's mouth, and the patient's cheeks. It is easy to appreciate why a patient would be uncomfortable with such a device installed. Moreover, installation of the rubber dam requires a substantial amount of skill. The hole must be punched in the proper location and the dam must be properly located in the patient's mouth.

A different kind of dental dam is disclosed in U.S. Pat. No. 3,772,790 to Swan-Gett et al. This dental dam is described as a tooth isolating shield having two hinged semi-rigid dentition bridge conforming members, each connected to a soft deformable apron. A layer of cushion deformable material lines each of the semi-rigid members. One of the semi-rigid members is molded or fitted to closely conform to a patient's upper arch and the other is molded or fitted to closely conform to a patient's lower arch. Spring wires are embedded in the semi-rigid members at their hinged connection to bias them apart from each other. The lower semi-rigid member is provided with a fluid conduit extending about its lower periphery. The conduit is provided with a plurality of spaced apart holes and a centrally located fitting for connection to an aspirator. Before installing the shield in a patient's mouth, the practitioner cuts an opening in the proper location on the shield to expose a particular tooth or group of teeth which will be treated.

The dental shield disclosed by Swan-Gett et al. must conform well to the patient's upper and lower arches so that it will be held in place during the procedure. In practice, however, close fitting of the shield with the arches is very difficult. Arch forms vary greatly in length, width, and shape (square to V-shaped). Moreover, misalignment of individual teeth hamper the fitting procedure. In addition, many patients have mismatched jaws, e.g. cross-bites in the anterior or porterior regions or overjets (buck teeth), which can preclude fitting this type of shield. At the very least, in order to accommodate a variety of patients, a very large stock of different sized shields must be maintained.

Because of the close fitting requirements of the Swan-Gett et al. shield, the time required to install the shield will be prolonged. Many trial and error attempts will have to be performed in order to find the right size shield for a particular patient. Each shield which is tried and not chosen must be re-sterilized or discarded, adding to the total cost of the procedure. Additional time is consumed by the marking and cutting of the shield to expose the operative tooth or teeth.

Swan-Gett et al. recommends that the shield be cut to expose the entire tooth, i.e. the buccal, occlusal, and lingual surfaces. However, exposure of the lingual surface is undesirable in a sealant application procedure since this exposes the tooth or teeth to contaminations. This is particularly so if more than one tooth is exposed. Theoretically, the shield could be cut to prevent lingual exposure, but this would require more time and great skill on the part of the practitioner. The close fitting requirement of the Swan-Gett et al. shield prevents access to the lingual surface without forfeiting isolation from the tongue.

Stability and retention of the Swan-Gett et al. shield depends chiefly on the cushion deformable material which lines the shield. The teeth, the cushion deformable material and the shield are all in intimate contact. Thus, water and air spray hitting these surfaces is deflected and creates an aerosol of contaminants which is aspirated only after the aerosol settles. The aerosol of contaminants poses a serious health risk to the practitioner. Some of the aerosol is deflected out of the patient's mouth and into the practitioner's face.

The Swan-Gett et al. shield is designed to hold the patient's mouth open with small springs in the hinges of the shield. However, this does not prevent the patient from biting and the patient must consciously avoid closing his/her mouth during the procedure.

Swan-Gett et al. provides an apron surrounding the shield to help direct fluid into the aspiration ports. The apron, however, tends to stretch the cheek mucosa of the patient and is quite irritating. In addition, the stretch cheek mucosa act on the apron to urge unseating of the shield.

All of these aspects of the Swan-Gett et al. shield also contribute to the overall bulkiness of the shield and resulting significant discomfort to the patient, and in particular to child patients.

SUMMARY OF THE INVENTION

It is therefore an object of the invention to provide a dental isolation tray for isolating teeth which includes an aspiration conduit to keep the isolated teeth dry.

It is also an object of the invention to provide a dental isolation tray which is effective in isolating a relatively large group (quadrant) of teeth.

It is another object of the invention to provide a dental isolation tray which does not require close fitting to the arches and does not require fitting both arches simultaneously.

It is still another object of the invention to provide a dental isolation tray which readily fits a variety of arches and can therefore be quickly installed by choosing from a small number of different sizes.

It is also an object of the invention to provide a dental isolation tray which allows access to the lingual surface of teeth while still isolating the lingual surface from the patient's tongue.

It is another object of the invention to provide a dental isolation tray which fits in the patient's mouth leaving ample space between the isolation tray and the teeth so that water and air spray is deflected by the tray into the space between the isolation tray and the teeth for aspiration.

It is yet another object of the invention to provide a dental isolation tray which allows the patient to comfortably bite while still maintaining the patient's mouth in the open position.

It is still another object of the invention to provide a dental isolation tray which is relatively compact and fits comfortably in the patient's mouth.

It is a further object of the invention to provide a dental isolation tray which is adjustable to fit different sized mouths and maintain the isolation tray in a comfortable but stable position.

In accord with these objects which will be discussed in detail below, the dental isolation tray of the present invention includes a single arch or quadrant tray which is constructed of a semi-rigid plastic material such as polypropylene. The tray has an outer side wall, an inner side wall, and a roof which joins the inner and outer side walls. An aspiration conduit having spaced apart aspiration ports is molded into the peripheral edges of the side walls and into the interface between the interior side wall and the roof. An aspiration coupling is provided for fluidly connecting the aspiration conduit with a suction tube. A portion of the roof and outer side wall is pre-cut to expose the occlusal and buccal aspects of preselected teeth. An adjustable bite block is mounted on or adjacent to the roof of the tray and extends substantially perpendicular to the roof of the tray. The full arch tray may have one or two quadrants cut-out and may be placed on either the upper or the lower arch to completely cover the arch and associated alveolar ridge. A single quadrant tray may be formed as either a left hand tray or a right hand tray and can also be placed over either upper or lower arches. The tray is dimensioned to provide relatively generous spacing between the side walls and the teeth so that the lingual aspect of the teeth which are exposed by the cut-out are accessible while still being isolated from the patient's tongue. The generous spacing of the tray allows for a quick fitting to any patient's mouth by selecting a tray from a relatively small number of different sizes. The tray is supported in the patient's mouth by the teeth which underlie the roof of the tray and by approximately two to three millimeters of tissue posterior of the molars which also underlies the roof of the tray. The tray is stabilized by the bite block which receives pressure from the patient's teeth which are opposite the teeth covered by the tray.

While the tray is particularly well suited for use in sealant procedures, the tray may also be used in other procedures with appropriate areas of the roof and outer side wall cut out. The presently preferred embodiment of the full arch tray has an extensible bite block mounted on the center of the interior wall. The bite block may also be rotationally mounted. The presently preferred embodiment of the quadrant tray has a removable bite block which snaps over the roof adjacent the quadrant cut out.

While a single tray may be placed on either the upper or lower arch, the invention also provides a modified tray which is specially designed for use over the upper arch. The upper arch tray includes a pair of rear supports which are formed by extending the height of the side walls posterior of the cut-outs and providing an angled roof over the extended side walls. The angle of the roof is such that the angled roof is substantially parallel to the lower arch when the patient's mouth is open. This angle also helps to collect sprayed water when the patient is in a reclined position.

The tray is easy to use in any procedure. The practitioner visually inspects the patient's mouth and chooses a tray for a small number of different sizes (typically small, medium, and large) and attaches a suction hose to the aspiration coupling. The patient opens his/her mouth. The practitioner inserts the tray with the hose attached. The patient bites down on the bite block. The cut-out portion of the tray can easily be enlarged using a lab separating disc on a dental handpiece drill. In a sealant operation, the patient's teeth are first pumiced clean. After the tray is installed, acid etchant is applied to the exposed teeth. The teeth are washed with a water spray which is suctioned off the teeth by the aspiration ports in the try. The teeth are further dried with an air spray. The sealant is then applied and allowed to cure. The tray is then removed and may be used on the opposite arch. Using a full arch tray with two cutouts, two quadrants may be sealed simultaneously.

Additional objects and advantages of the invention will become apparent to those skilled in the art upon reference to the detailed description taken in conjunction with the provided figures.

BRIEF DESCRIPTION OF THE DRAWINGS

FIG. 5 is a perspective view of a half-arch tray according to the invention;

FIG. 6 is a broken perspective view of another embodiment of a bite block;

FIG. 7 is a perspective view of a full arch tray with the bite block of FIG. 6; and FIG. 8 is a cross sectional view along line 8—8 in FIG. 7 showing how the spacing of the side walls deflects fluid spray.

DETAILED DESCRIPTION OF THE PREFERRED EMBODIMENTS

Figure 1:
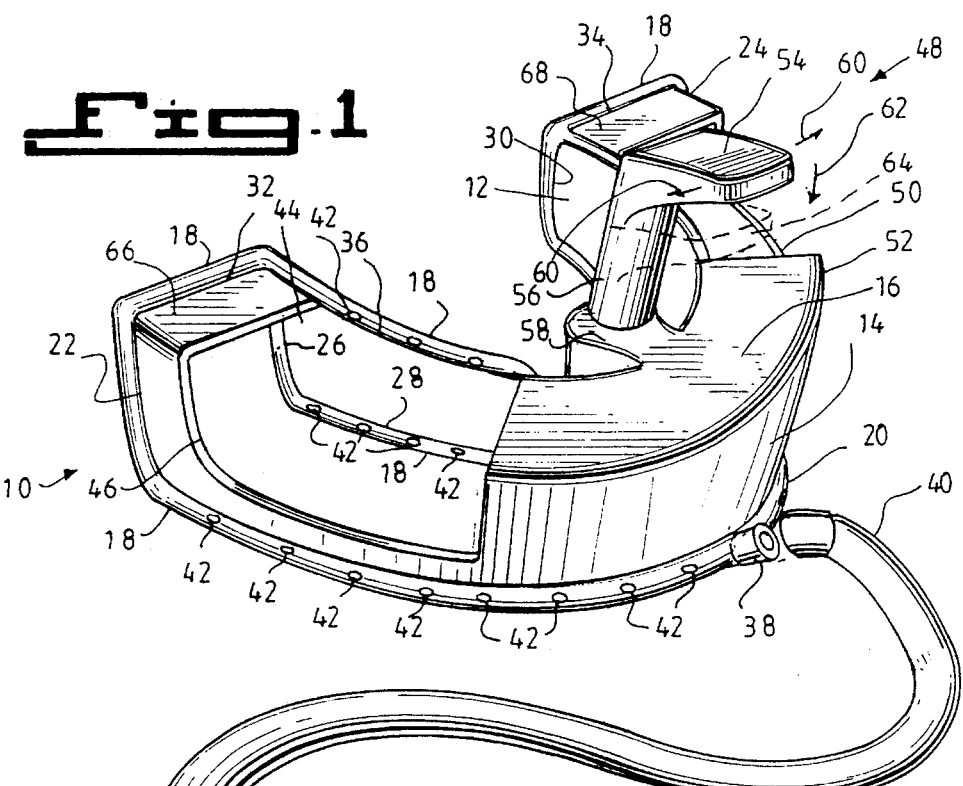
FIG. 1 is a perspective view of a full arch tray according to the invention showing two quadrant cut-outs.

Turning now to FIG. 1, the dental isolation tray 10 of the invention includes a generally U-shaped member formed by an inner side wall 12, and outer side wall 14, and a roof 16. A fluid conduit 18 is preferably located along the peripheral edges 20, 22, and 24 of the outer side wall 14, the peripheral edges 26, 28, and 30 of the inner side wall 12, the posterior edges 32, 34 of the roof 16, and along at least a portion of the interface 36 between the inner side wall 12 and the roof 16. The fluid conduit 18 is provided with a fluid coupling 38 for connection with an aspiration hose 40 and a plurality of spaced aspiration ports 42 are provided on at least a portion of the fluid conduit 18. At least one portion 44 of the roof 16 is cut away as is an adjacent portion 46 of the outer side wall 14. A bite block 48 is mounted on or adjacent to a central portion of the roof 16. As shown in FIG. 1, a second portion 50 of the roof 16 and an adjacent portion 52 of the outer side wall 14 is also cut away. The bite block 48, shown in FIG. 1, is a substantially L-shaped member having a biting surface 54 and a contiguous stem 56. The stem 56 is extensibly mounted in a central hub 58 which is located on a central portion of the inner side wall 12 adjacent to the roof 16. The biting surface 54 is movable up and down relative to the roof 16 as indicated by the arrow 62 and the phantom lines 64. It may be desirable to mount the bite block so that it is rotatable left and right as shown by the arrows 60, but it is not necessary to do so. The bite block stem 56 may be friction fitted in the hub 58 or a modified bayonet-type mounting may be used.

Figure 2:
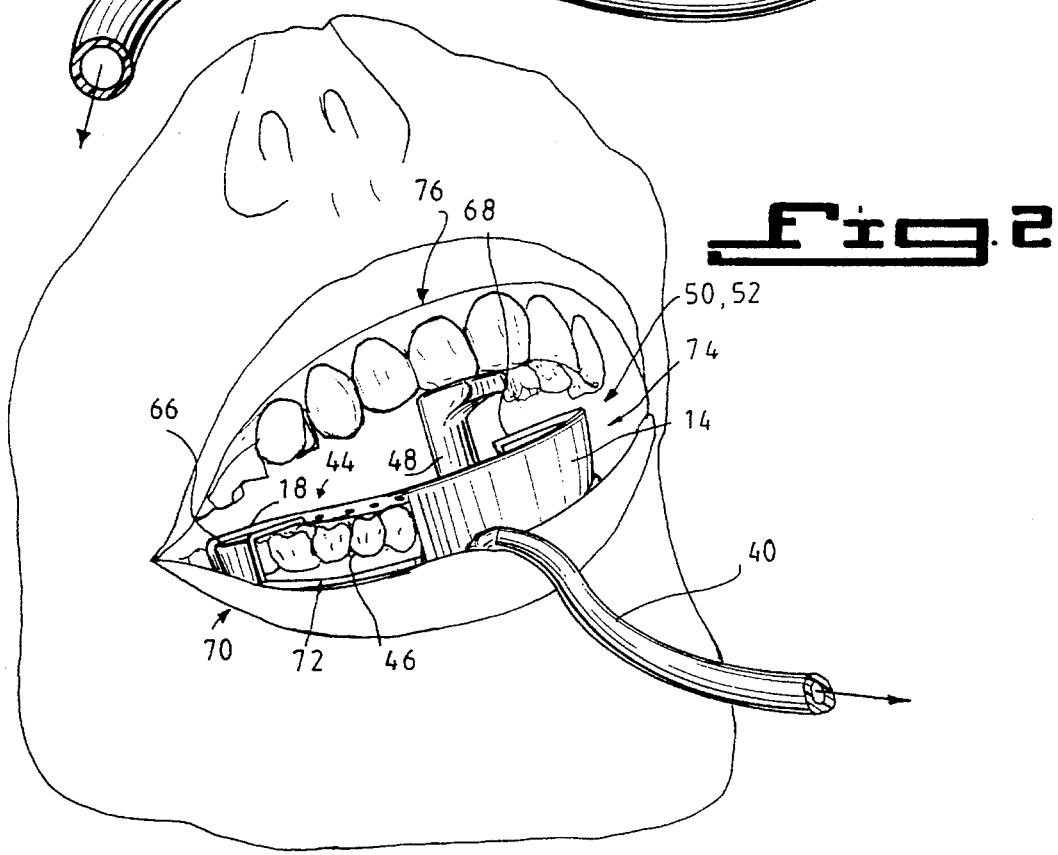
FIG. 2 is a perspective view of the tray of FIG. 1 installed in a patient's mouth.

The isolation tray 10 shown in FIG. 1 is a full arch tray designed to fit over the entire upper or lower arch and associated alveolar ridge of a patient as shown, for example, in FIG. 2 where the tray 10 is placed over the a patient's lower arch 70. When in place, the cut-out portions 44, 46, 50 and 52 are positioned to overlie opposite quadrants 72, 74 of the lower arch 70. Notably, end portions 66, 68 of the roof 16 posterior of the cut out portions are positioned to overlie tissue posterior of the molars. As seen in FIG. 2, the upper incisors 76 engage the bite block 48 to stabilize the tray and keep the patient's mouth open.

Figure 3:
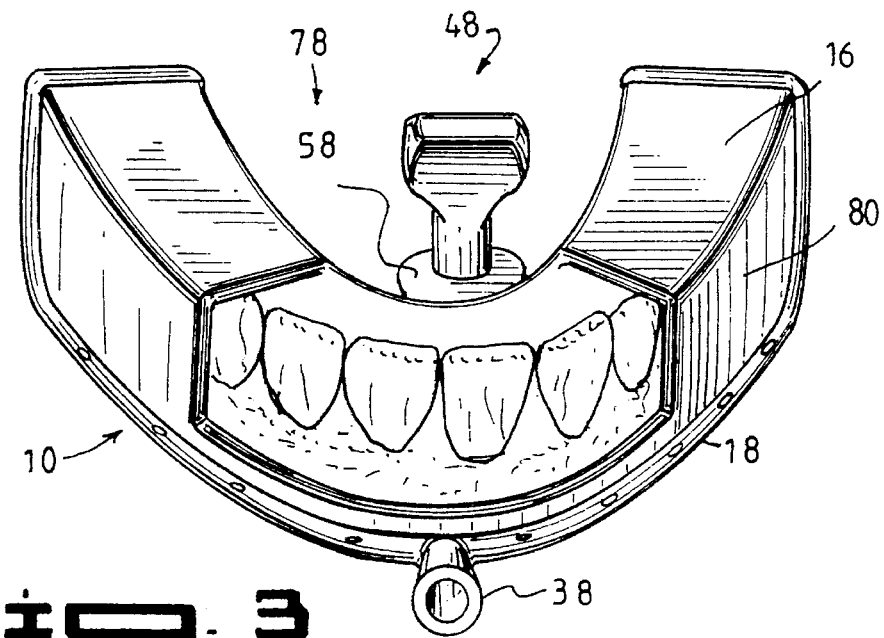
FIG. 3 is a perspective view of a tray according to the invention having a single central cut-out.

Turning now to FIG. 3, it will be appreciated that the dental isolation tray 10 may be configured to isolate any teeth, not just the quadrants. As shown in FIG. 3, a central portion 78 of the roof 16 and an adjacent portion 80 of the outer side wall 14 are cut away to expose the incisors. While this tray and the tray described above with reference to FIGS. 1 and 2 may be used on either the upper or lower arch, a specially designed upper arch tray may be provided as described below with reference to FIG. 4.

Figure 4:
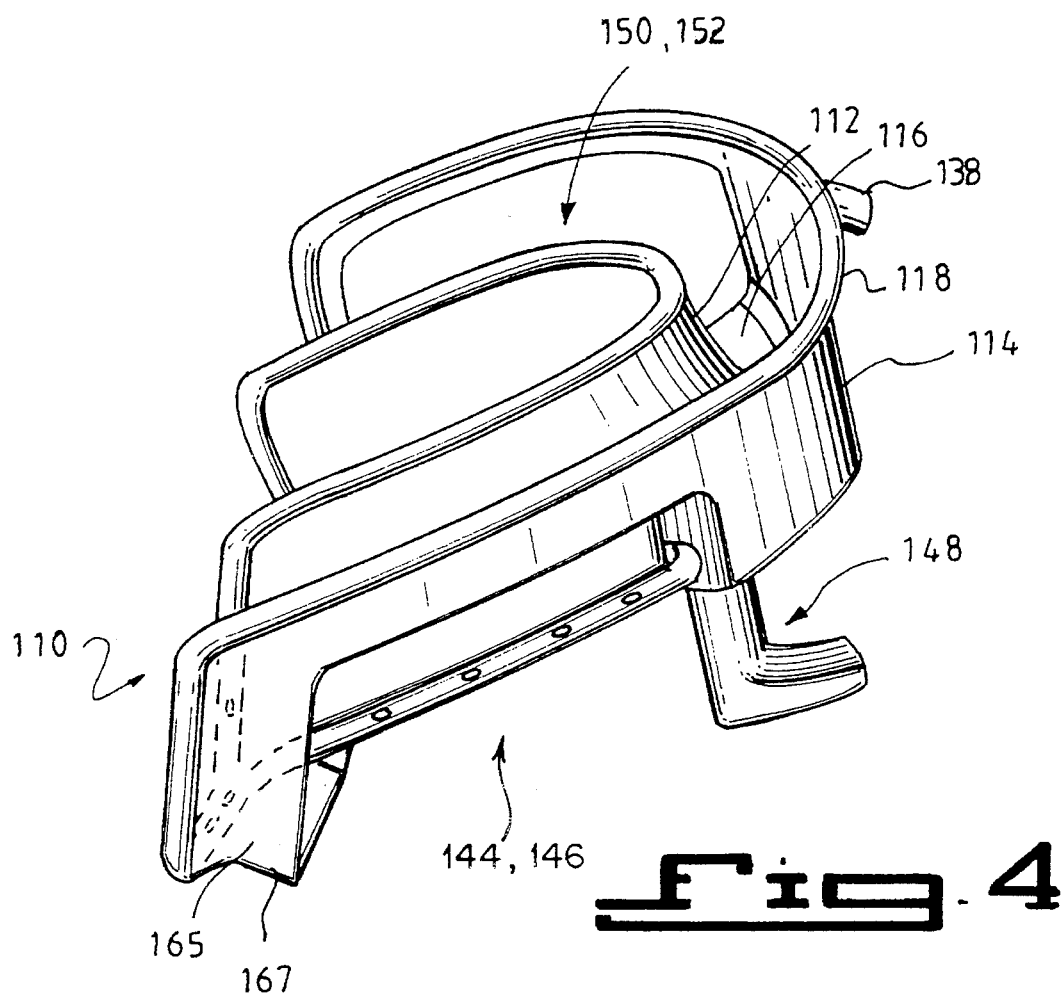
FIG. 4 is a view similar to FIG. 1 of another embodiment of the tray with a modified structure especially suited for use on the upper arch.

FIG. 4 shows a slightly different isolation tray 110. The tray 110 has many elements similar to the tray 10 which are numbered with similar reference numerals increased by 100. In this tray, however, end portions of the inner side wall 112 and outer side wall 114 are slightly higher as shown generally by numeral 165 posterior of the cut-outs 144, 146 and 150, 152. In addition, the portions of the roof 116 which is contiguous with the extended side walls 165 is angled as shown generally by numeral 167. From the foregoing, those skilled in the art will appreciate that when the tray 110 in placed over the upper arch of a patient, the angled portions 167 of the roof 116 will overlie the tissue posterior of the lower molars providing additional contour to collect fluid when the patient is in a reclined position.

As mentioned briefly above, the isolation tray may be a full arch tray or a half-arch tray. FIG. 5 shows an example of a half-arch tray 210 according to the invention. This tray is substantially the same as the tray 10 described above and is pictured with similar reference numerals, increased by 200, referring to similar elements of the tray. Tray 210 is substantially one half the size of the tray 10 described above. That is, for example, approximately half of the tray on one side of the bite block 248 is missing. The tray 210 is useful in procedures where only one quadrant or other teeth in one half of an arch is to be isolated.

Depending on the requirements of a particular dental procedure, the bite block of the isolation tray may be configured in different ways. An example of a different type of bite block 348 is shown in FIGS. 6 and 7. The isolation tray 310 is substantially the same as the tray 10 described above and is pictured with similar reference numerals, increased by 300, referring to similar elements of the tray. Tray 310, however, does not utilize the bite block hub 358 and it may even be omitted during manufacture, if desired. The bite block 348 is designed to directly engage a portion of the roof 316 adjacent a cut-out portion 344 or 350. The bite block 348 is thus formed with an upper biting surface 354, a contiguous stem 356 and a lower roof engaging slot 357. As shown in FIGS. 6 and 7, the bite block 348 may be attached to either of the posterior roof portions 366 or 368. Those skilled in the art will appreciate, however, that the roof engaging slot 357 in the bite block 348 may be configured to engage any edge portion of the roof 316 which is adjacent a cut-out portion.

As mentioned briefly above, the spacing of the inner and outer side walls helps to deflect fluid spray into the space between the teeth and the side walls. FIG. 8 illustrates how fluid 400 from a fluid jet 402, such as an irrigation or air spray, is deflected by the side walls 312, 314 into the spaces between the teeth and the side walls.

There have been described and illustrated herein several embodiments of a dental isolation tray. While particular embodiments of the invention have been described, it is not intended that the invention be limited thereto, as it is intended that the invention be as broad in scope as the art will allow and that the specification be read likewise. Thus, while particular materials have been disclosed, it will be appreciated that other materials could be utilized to manufacture the tray. Also, while different removable bite blocks have been shown, it will be recognized that other types of bite blocks, including non-removable bite blocks could be used with similar results obtained. Moreover, while particular configurations have been disclosed in reference to the aspiration conduit, it will be appreciated that other configurations could be used as well. Furthermore, while the tray has been disclosed as being sized to fit a full arch or a half arch, it will be understood that different sized trays can achieve the same or similar function as disclosed herein.

It will therefore be appreciated by those skilled in the art that yet other modifications could be made to the provided invention without deviating from its spirit and scope as so claimed.

I claim:

1. A dental isolation tray for use with a single arch in a patient's mouth comprising:

a) an inner side wall;

b) an outer side wall;

c) a roof joining said inner side wall and said outer side wall;

d) a fluid conduit extending along a peripheral portion of one of said inner side wall and said outer side wall, said fluid conduit having a plurality of fluid ports and a fluid coupling for coupling said fluid conduit with an aspiration hose, wherein a portion of said roof and a portion of said side wall adjacent said portion of said roof being capable of being cut-away to expose at least a portion of the patient's arch for treatment, and said tray is dimensioned to fit comfortably over one of an upper arch, a lower arch, an upper quadrant, and a lower quadrant such that teeth are substantially covered by said roof, said inner side wall, and said outer side wall while maintaining unfilled space between said teeth and said sidewalls to allow for the deflection by said tray of the water and air spray into the space between the isolation tray and the teeth for aspiration; and e) a bite block extending substantially orthogonal to said roof which is engageable with the opposite arch in the patient's mouth so as to comfortably maintain the patient's mouth in an open position.

2. A dental isolation tray according to claim 1, wherein: said fluid conduit extends along an interface between said inner side wall and said roof.

3. A dental isolation tray according to claim 1, wherein: said inner wall, said outer wall, and said roof form a substantially U-shaped structure having a substantially U-shaped cross section.

4. A dental isolation tray according to claim 1, wherein: said bite block comprises a substantially L-shaped member.

5. A dental isolation tray according to claim 4, wherein: said bite block comprises a substantially flat biting surface and a contiguous stem.

6. A dental isolation tray according to claim 5, wherein: one of said inner side wall and said outer side wall is provided with an adjacent hub for receiving said stem of said bite block.

7. A dental isolation tray according to claim 6, additionally including means for adjustably positioning said stem of said bite block in said hub.

8. A dental isolation tray according to claim 1, wherein: said bite block is removable from said isolation tray.

9. A dental isolation tray according to claim 8, wherein: said bite block has an upper biting surface and a lower roof engaging slot.

10. A dental isolation tray according to claim 1, wherein: posterior end portions of said inner side wall and said outer side wall are extended in height, and posterior end portions of said roof adjacent said posterior end portions of said inner side wall and said outer side wall include angled portions such that when said isolation tray is placed over an upper arch, said angled portions are substantially parallel to a lower arch.

11. A method of using a dental isolation tray having an inner side wall, an outer side wall, a roof joining the inner side wall and the outer side wall, a bite block extending substantially orthogonal to the roof, and a fluid conduit extending along a peripheral portion of one of the inner side wall and the outer side wall, the fluid conduit having a plurality of fluid ports and a fluid coupling for coupling the fluid conduit with an aspiration hose, said method comprising:

a) removing a portion of the outer side wall and an adjacent portion of the roof;

b) attaching an aspiration hose to the fluid coupling;

c) placing the dental isolation tray in a patient's mouth over a single arch so that some teeth are covered by the side walls and the roof of the tray and that at least one tooth is exposed by the portion of the roof and outer side wall which were removed while maintaining unfilled space between said teeth and said sidewalls to allow for the deflection by said tray of the water and air spray into the space between the isolation tray and the teeth for aspiration;

d) positioning said bite block in the patient's mouth such that the patient may bite on the bite block to stabilize the tray in the patient's mouth;

e) performing a dental procedure on the at least one tooth which is exposed; and f) removing the dental isolation tray from the patient's mouth.

12. A method of using a dental isolation tray having an inner side wall, an outer side wall, a roof joining the inner side wall and the outer side wall, a bite block extending substantially orthogonal to the roof, and a fluid conduit extending along a peripheral portion of one of the inner side wall and the outer side wall, the fluid conduit having a plurality of fluid ports and a fluid coupling for coupling the fluid conduit with an aspiration hose, said method comprising:

a) removing a portion of the outer side wall and an adjacent portion of the roof;

b) attaching an aspiration hose to the fluid coupling;

c) placing the dental isolation tray in a patient's mouth over an arch so that some teeth are covered by the side walls and the roof of the tray and that at least one tooth is exposed by the portion of the roof and outer side wall which were removed;

d) directing the patient to bite on the bite block to stabilize the tray in the patient's mouth;

e) activating a vacuum source coupled to the aspiration hose;

f) applying an acid etchant to all surfaces of the at least one exposed tooth;

g) washing the etchant off the at least one exposed tooth;

h) drying the at least one exposed tooth with an air spray;

i) applying a dental sealant to the at least one exposed tooth;

j) allowing the sealant to cure; and k) removing the dental isolation tray from the patient's mouth.

13. A method according to claim 12, wherein: said step of removing a portion is performed during the manufacture of the dental isolation tray.

14. A method according to claim 12, wherein: said portion of said outer side wall corresponds to a quadrant of teeth.

15. A dental isolation tray for use with one arch in a patient's mouth comprising:

a) an inner side wall;

b) an outer side wall;

c) a roof joining said inner side wall and said outer side wall;

d) a fluid conduit extending along a peripheral portion of one of said inner side wall and said outer side wall, said fluid conduit having a plurality of fluid ports and a fluid coupling for coupling said fluid conduit with an aspiration hose; and e) a bite block extending substantially orthogonal to said roof, wherein
a portion of said roof and a portion of said side wall adjacent said portion of said roof is capable of being cut-away to expose at least a portion of the patient's arch for treatment, and
said tray is dimensioned to fit over one of an upper arch, a lower arch, an upper quadrant, and a lower quadrant such that the patient's teeth are substantially covered by said roof, said inner side wall, and said outer side wall and said tray is stabilized by said bite block.

16. A dental isolation tray according to claim 15, wherein: said bite block is removable from said tray.

17. A dental isolation tray according to claim 15, additionally including means for adjustably positioning said bite block relative to said roof.

18. A dental isolation tray according to claim 15, wherein:

said bite block comprises a substantially L-shaped member having an upper flat surface and a contiguous stem, and one of said inner side wall and said outer side wall is provided with an adjacent hub for receiving said contiguous stem.

19. A dental isolation tray according to claim 15, wherein:

said bite block has a substantially flat upper biting surface and a substantially parallel lower roof engaging slot, and said bite block is removably coupled to a portion of said roof.

20. A dental isolation tray comprising:

a) an inner side wall;
b) an outer side wall;
c) a roof joining said inner side wall and said outer side wall; and
d) a fluid conduit extending along a peripheral portion of one of said inner side wall and said outer side wall and along an interface between said inner side wall and said roof, said fluid conduit having a plurality of fluid ports and a fluid coupling for coupling said fluid conduit with an aspiration hose, wherein
 a portion of said roof and a portion of said side wall adjacent said portion of said roof is capable of being cut-away, and
 said tray is dimensioned to fit comfortably over one of an upper arch, a lower arch, an upper quadrant, and a lower quadrant such that teeth are substantially covered by said roof, said inner side wall, and said outer side wall while maintaining unfilled space between said teeth and said inner side wall.

21. A dental isolation tray comprising:

a) an inner side wall;
b) an outer side wall;
c) a roof joining said inner side wall and said outer side wall;
d) a fluid conduit extending along a peripheral portion of one of said inner side wall and said outer side wall, said fluid conduit having a plurality of fluid ports and a fluid coupling for coupling said fluid conduit with an aspiration hose; and
e) a bite block extending substantially orthogonal to said roof, said bite block comprising a substantially L-shaped member having a substantially flat biting surface and a contiguous stem, and wherein one of said inner side wall and said outer side wall is provided with an adjacent hub for receiving said stem of said bite block, and wherein
 a portion of said roof and a portion of said side wall adjacent said portion of said roof is capable of being cut-away, and
 said tray is dimensioned to fit comfortably over one of an upper arch, a lower arch, an upper quadrant, and a lower quadrant such that teeth are substantially covered by said roof, said inner side wall, and said outer side wall while maintaining unfilled space between said teeth and said inner side wall to allow for the deflection by said tray of the water and air spray into the space between the isolation tray and the teeth for aspiration.

22. A dental isolation tray comprising:

a) an inner side wall;
b) an outer side wall;
c) a roof joining said inner side wall and said outer side wall; and
d) a fluid conduit extending along a peripheral portion of one of said inner side wall and said outer side wall, said fluid conduit having a plurality of fluid ports and a fluid coupling for coupling said fluid conduit with an aspiration hose, and
e) a bite block extending substantially orthogonal to said roof, said bite block having an upper biting surface and a lower roof engaging slot and said bite block being removable from said isolating tray, and wherein
 a portion of said roof and a portion of said side wall adjacent said portion of said roof is capable of being cut-away, and
 said tray is dimensioned to fit comfortably over one of an upper arch, a lower arch, an upper quadrant, and a lower quadrant such that teeth are substantially covered by said roof, said inner side wall, and said outer side wall while maintaining unfilled space between said teeth and said inner side wall.

23. A dental isolation tray comprising:

a) an inner side wall;
b) an outer side wall;
c) a roof joining said inner side wall and said outer side wall; and
d) a fluid conduit extending along a peripheral portion of one of said inner side wall and said outer side wall, said fluid conduit having a plurality of fluid ports and a fluid coupling for coupling said fluid conduit with an aspiration hose, wherein
 a portion of said roof and a portion of said side wall adjacent said portion of said roof is capable of being cut-away,
 said tray is dimensioned to fit comfortably over one of an upper arch, a lower arch, an upper quadrant, and a lower quadrant such that teeth are substantially covered by said roof, said inner side wall, and said outer side wall while maintaining unfilled space between said teeth and said inner side wall, and
 posterior end portions of said inner side wall and said outer side wall are extended in height, and posterior end portions of said roof adjacent said posterior end portions of said inner side wall and said outer side wall including angled portions such that when said isolation tray is placed over an upper arch, said angled portions are substantially parallel to a lower arch.

24. A dental isolation tray comprising:

a) an inner side wall;
b) an outer side wall;
c) a roof joining said inner side wall and said outer side wall; and
d) a fluid conduit extending along a peripheral portion of one of said inner side wall and said outer side well, said fluid conduit having a plurality of fluid ports and a fluid coupling for coupling said fluid conduit with an aspiration hose; and
e) a bite block extending substantially orthogonal to said roof, said bite block comprising a substantially L-shaped member having an upper flat surface and a contiguous stem, and one of said inner side wall and said outer side wall is provided with an adjacent hub for receiving said contiguous stem, wherein a portion of said roof and a portion of said side wall adjacent said portion of said roof is capable of being cut-away, and said tray is dimensioned to fit over one of an upper arch, a lower arch, an upper quadrant, and a lower quadrant such that teeth are substantially covered by said roof, and said inner side wall, and said outer side wall and said tray is stabilized by said bite block.

25. A dental isolation tray comprising:
a) an inner side wall;
b) an outer side wall;
c) a roof joining said inner side wall and said outer side wall;
d) a fluid conduit extending along a peripheral portion of one of said inner side wall and said outer side well, said fluid conduit having a plurality of fluid ports and a fluid coupling for coupling said fluid conduit with an aspiration hose; and
e) a bite block extending substantially orthogonal to said roof, said bite block having a substantially flat upper biting surface and a substantially parallel lower roof engaging slot, and said bite block being removably coupled to a portion of said roof, wherein a portion of said roof and a portion of said side wall adjacent said portion of said roof is capable of being cut-away, and said tray is dimensioned to fit over one of an upper arch, a lower arch, an upper quadrant, and a lower quadrant such that teeth are substantially covered by said roof, and said inner side wall, and said outer side wall and said tray is stabilized by said bite block.

* * * * *